US011105799B2

(12) United States Patent
Glezer et al.

(10) Patent No.: US 11,105,799 B2
(45) Date of Patent: Aug. 31, 2021

(54) BIOMARKERS OF THERAPEUTIC RESPONSIVENESS

(71) Applicant: Meso Scale Technologies, LLC., Rockville, MD (US)

(72) Inventors: Eli N. Glezer, Del Mar, CA (US); Anu Mathew, North Potomac, MD (US)

(73) Assignee: Meso Scale Technologies, LLC., Rockville, MD (US)

( * ) Notice: Subject to any disclaimer, the term of this patent is extended or adjusted under 35 U.S.C. 154(b) by 0 days.

(21) Appl. No.: 15/813,411

(22) Filed: Nov. 15, 2017

(65) Prior Publication Data

US 2018/0088108 A1 Mar. 29, 2018

Related U.S. Application Data

(60) Division of application No. 13/966,963, filed on Feb. 3, 2014, now abandoned, which is a continuation-in-part of application No. 13/318,174, filed as application No. PCT/US2010/032879 on Apr. 29, 2010, now abandoned.

(60) Provisional application No. 61/215,071, filed on May 1, 2009.

(51) Int. Cl.
  *G01N 33/574* (2006.01)
  *G01N 33/543* (2006.01)

(52) U.S. Cl.
  CPC ..... *G01N 33/543* (2013.01); *G01N 33/57438* (2013.01); *G01N 2800/52* (2013.01)

(58) Field of Classification Search
  CPC combination set(s) only.
  See application file for complete search history.

(56) References Cited

U.S. PATENT DOCUMENTS

| | | | |
|---|---|---|---|
| 4,168,146 | A | 9/1979 | Grubb et al. |
| 4,235,601 | A | 11/1980 | Deutsch et al. |
| 4,366,241 | A | 12/1982 | Tom et al. |
| 4,442,204 | A | 4/1984 | Greenquist et al. |
| 5,208,535 | A | 5/1993 | Nakayama et al. |
| 5,807,522 | A | 9/1998 | Brown et al. |
| 6,110,426 | A | 8/2000 | Shalon et al. |
| 2003/0113713 | A1 | 6/2003 | Glezer et al. |
| 2003/0207290 | A1 | 11/2003 | Kenten et al. |
| 2004/0022677 | A1 | 2/2004 | Wohlstadter et al. |
| 2004/0189311 | A1 | 9/2004 | Glezer et al. |
| 2005/0052646 | A1 | 3/2005 | Wohlstadter et al. |
| 2005/0142033 | A1 | 6/2005 | Glezer et al. |
| 2006/0205012 | A1 | 9/2006 | Debad et al. |
| 2010/0099109 | A1* | 4/2010 | Fantl ................. G01N 33/5041 435/6.11 |
| 2012/0046197 | A1 | 2/2012 | Glezer et al. |
| 2014/0141985 | A1 | 5/2014 | Glezer et al. |

FOREIGN PATENT DOCUMENTS

| | | |
|---|---|---|
| WO | 99/26067 A1 | 5/1999 |
| WO | 2004/058055 A2 | 7/2004 |
| WO | 2007/040559 A2 | 4/2007 |

OTHER PUBLICATIONS

Sourbier et al (Cancer Research, 2006, 66:5130-5142).*
Gowan et al (Assay and Drug Development Technologies, 2007, 5:391-401).*
Grund et al (Molecular Pharmacology, 2008, 73:1394-1404).*
Shiota et al (International J Oncology, 2010, 37:509-517).*
Goncharenko-Khaider et al (Oncogene, 2010, 29:5523-5536).*
Adnane et al (Methods in Enzymology, 2006, 407:597-612).*
Murphy et al (American Journal of Pathology, 2006, 169:1875-1885).*
Liu et al (Cancer Research, 2006, 66:11851-11858).*
Wako BioWindow (http://www.wako-chem.co.jp) published Aug. 2008.*
Bachelder R.E. et al., "Vascular Endothelial Growth Factor is an Autocrine Survival Factor for Neuropilin-Expressing Breast Carcinoma Breast Carcinoma Cells", Cancer Research 61(15):5736-5740 (Aug. 1, 2001).
Berns A., "Gene Expression in Diagnosis", Cancer 403:491-492 (2000).
Chang Y.S. et al., "Sofafenib (BAY 43-9006) Inhibits Tumor Growth and Vascularization and Induces Tumor Apoptosis and Hypoxia in RCC Xenograft Models", Cancer Chemother Pharmacol 59(5):561-574 (2007).
Chen R. et al., "Simultaneous Quantification of Six Human Cytokines in a Single Sample Using Microparticle-Based Flow Cytometric Technology", Clinical Chemistry 45(9):1693-1694 (1999).
Chen Z. et al., "Crucial Role of p53-Dependent Cellular Senescence in Suppression of Pten-Deficient Tumorigenesis", Nature 436:725-730 (Aug. 4, 2005).
Delehanty J.B., "Printing Functional Protein Microarrays Using Piezoelectric Capillaries", Methods in Molecular Biology 264:135-143 (2004).
Fan Y. et al., "An Antisense Oligodeoxynucleotide to p21Waf1/Cip1 Causes Apoptosis in Human Breast Cancer Cells", Molecular Cancer Therapeutics 2(8):773-782 (Aug. 2003).
Garcia J.A. et al., "Recent Progress in the Management of Advanced Renal Cell Carcinoma", CA A Cancer Journal for Clinicians 57(2):112-125 (2007).
Garcia J.A. et al., "Renal Cell Carcinoma", Current Opinion in Oncology 21:266-271 (2009).
Gimenez S.E. et al., "Prognostic Markers and Targeted Therapies for Renal Cell Carcinoma", Future Oncology 5 (2):197-205 (2009).
Gowan S.M. et al., "Application of Meso Scale Technology for the Measurement of Phosphoproteins in Human Tumor Xenografts", Assay and Drug Development Technologies 5(3):391-401 (2007).

(Continued)

*Primary Examiner* — Laura B Goddard
(74) *Attorney, Agent, or Firm* — Scully, Scott, Murphy & Presser, P.C.

(57) ABSTRACT

The present invention relates to methods of diagnosing a kidney disorder in a patient, as well as methods of monitoring the progression of a kidney disorder and/or methods of monitoring a treatment protocol of a therapeutic agent or a therapeutic regimen. The invention also relates to assay methods used in connection with the diagnostic methods described herein.

13 Claims, 3 Drawing Sheets

(56) References Cited

OTHER PUBLICATIONS

Grund E.M. et al., "Tumor Necrosis Factor-a Regulates Inflammatory and Mesenchymal Responses Via Mitogen-Activated Protein Kinase Kinase, p38, and Nuclear Factor kB in Human Endometriotic Epithelial Cells", Molecular Pharmacology 73(5):1394-1404 (2008).
Horiguchi A. et al., "Elevated AKT Activation and its Impact on Clinicopathological Features of Renal Cell Carcinoma", The Journal of Urology 169(2):710-713 (Feb. 2003).
Jung J.E. et al., "STAT3 is Potential Modulator of HIF-1-Mediated VEGF Expression in Human Renal Carcinoma Cells", The FASEB Journal 19(10), pp. 1-18 (2005).
Khan I.H. et al., "Multiplex Analysis of Intracellular Signaling Pathways in Lymphoid Cells by Microbead Suspension Arrays", Molecular & Cellular Proteomics 5.4:758-768 (2006).
Kummar S. et al., "Compressing Drug Development Timelines in Oncology Using Phase '0' Trials", Nature Reviews Cancer 7(2):131-139 (Feb. 2007).
Lane B.R. et al., "Prognostic Models and Algorithms in Renal Cell Carcinoma", Urol Clin N Am 35:613-625 (2008).
Lee T-H et al., "Vascular Endothelial Growth Factor Mediates Intracrine Survival in Human Breast Carcinoma Cells Through Internally Expressed VEGFR1/FLT1", PloS Medicine 4(6):1101-1116 (Jun. 2007).
Li Y. et al., "AKT/PKB Phosphorylation of p21Cip/WAF1 Enhances Protein Stability of p21Cip/WAF1 and Promotes Cell Survival", The Journal of Biological Chemistry 277(13):11352-11361 (Mar. 29, 2002).
Ljunberg B., "Prognostic Markers in Renal Cell Carcinoma", Current Opinion in Urology 17:303-308 (2007).
Lovett R.A., "Toxicogenomics: Toxicologists Brace for Genomics Revolution", Science 289(5479):536-537 (2000).
Lue R.Y.P. et al., "Site-Specific Immobilization of Biotinylated Proteins for Protein Microarray Analysis", Methods in Molecular Biology 264:85-100 (2004).
Masood R. et al., "Vascular Endothelial Growth Factor (VEGF) in an Autocrine Growth Factor for VEGF Receptor-Positive Human Tumors", Blood 98(6):1904-1913 (Sep. 15, 2001).
Miyata Y. et al., "Presence of Phosphorylated Hepatocyte Growth Factor Receptor/c-Met is Associated with Tumor Progression and Survival in Patients with Conventional Renal Cell Carcinoma", Clin Cancer Research 12 (16):4876-4881 (Aug. 15, 2006).
Motoshima H. et al., "AMPK and Cell Proliferation—AMPK as a Therapeutic Target for Atherosclerosis and Cancer", J Physiol 574.1:63-71 (2006).
Murphy D.A. et al., "Inhibition of Tumor Endothelial ERK Activation, Angiogenesis, and Tumor Growth by Sorafenib (BAY43-9006)", The American Journal of Pathology 169(5):1875-1885 (Nov. 2006).
Nagata D. et al., "AMP-Activated Protein Kinase (AMPK) Signaling in Endothelial Cells is Essential for Angiogenesis in Response to Hypoxic Stress", The Journal of Biological Chemistry 278(33):31000-31006 (Aug. 2003).
Panka D.J. et al., "GSK-3β Inhibition Enhances Sorafenib-Induced Apoptosis in Melanoma Cell Lines", The Journal of Biological Chemistry 283(2):726-732 (Jan. 11, 2008).
Park M.K. et al., "A Latex Bead-Based Flow Cytometric Immunoassay Capable of Simultaneous Typing of Multiple Pneumococcal Serotypes (Multibead Assay)", Clinical and Diagnostic Laboratory Immunology 7(3):486-489 (2000).
Rini B.I., "Vascular Endothelial Growth Factor-Targeted Therapy in Renal Cell Carcinoma: Current Status and Future Directions", Clin Cancer Research 13(4):1098-1106 (Feb. 15, 2007).
Skates S.J. et al., "Pooling of Case Specimens to Create Standard Serum Sets for Screening Cancer Biomarkers", Cancer Epidemiol Biomarkers Prev. 16(2):334-341 (2007).
Tunuguntla H.S.G.R. et al., "Diagnostic and Prognostic Molecular Markers in Renal Cell Carcinoma", The Journal of Urology 179:2096-2102 (Jun. 2008).
Vignali D.A.A., "Multiplexed Particle-Based Flow Cytometric Assays", Journal of Immunological Methods 243:243-255 (2000).
Walt D.R., "Molecular Biology: Bead-Based Fiber-Optic Arrays", Science 287(5452):451-452 (2000).
Waltenberger J. et al., "Different Signal Transduction Properties of KDR and Flt1, Two Receptors for Vascular Endothelial Growth Factor", The Journal of Biological Chemistry 269(43):26988-26995 (Oct. 1994).
Weiss R.H. et al., "p21 is a Prognostic Marker for Renal Cell Carcinoma: Implications for Novel Therapeutic Approaches", The Journal of Urology 177(1):63-69 (Jan. 2007).
Weiss R.H., "p21Waf1/Cip1 as a Therapeutic Target in Breast and Other Cancers", Cancer Cell 4(6):425-429 (Dec. 2003).
Wilhelm S.M. et al., "BAY 43-9006 Exhibits Broad Spectrum Oral Antitumor Activity and Targets the RAF/MEK/ERK Pathway and Receptor Tyrosine Kinases Involved in Tumor Progression and Angiogenesis", Cancer Research 64 (19):7099-7109 (Oct. 1, 2004).
Final U.S. Office Action dated Aug. 22, 2017 received in U.S. Appl. No. 13/966,963.
U.S. Office Action dated Feb. 6, 2017 received in U.S. Appl. No. 13/966,963.
Final U.S. Office Action dated Feb. 2, 2016 received in U.S. Appl. No. 13/966,963.
U.S. Office Action dated May 22, 2015 received in U.S. Appl. No. 13/966,963.

\* cited by examiner

BIOMARKERS OF THERAPEUTIC RESPONSIVENESS

CROSS REFERENCE TO RELATED APPLICATIONS

The present application is a divisional of co-pending application having U.S. Ser. No. 13/966,963, filed on Feb. 3, 2014, which is a continuation-in-part of co-pending application having U.S. Ser. No. 13/318,174, filed on Oct. 31, 2011, which is a 371 of International Application having Serial No. PCT/US2010/032879, filed on Apr. 29, 2010, which claims benefit of U.S. Provisional Application No. 61/215,071, filed on May 1, 2009, the contents of all of which are incorporated herein by reference.

STATEMENT REGARDING FEDERALLY-SPONSORED RESEARCH

This invention was made with government support under HHSN261200700051C awarded by the National Institutes of Health. The government has certain rights in the invention.

FIELD OF THE INVENTION

This application relates to assay methods useful in the detection and treatment of renal cell carcinoma (RCC).

BACKGROUND OF THE INVENTION

Challenges in the field of oncology include the lack of efficient means for early cancer detection and for specific cancer subtyping and for measuring and/or predicting responsiveness to therapy. There is a need for new cancer biomarkers that can provide early and specific diagnosis of cancer and enable targeted therapy and prognosis. The need for new diagnostics has been the impetus behind many initiatives targeting the discovery and development of new biomarkers for cancer. The hope is that the identification of suitable biomarkers will allow for the development of early cancer detection screening tests and will lead to improved cancer therapy and a reduction in the mortality associated with many cancers.

Kinases are specialized proteins that function within intracellular communication networks known as signal transduction pathways. Preclinical studies have shown that these pathways are important in the development of tumor vasculature and in the proliferation of tumor cells, leading to tumor growth and metastases. Therefore, by blocking the kinases involved in these signaling pathways, tumor growth and proliferation may be controlled. Kinases are located on multiple levels of signaling pathways. Receptor tyrosine kinases are located upstream in the signaling pathway of tumor vasculature (e.g., VEGFR and PDGFR) and tumor cells (e.g., Kit and FLT-3). Serine/threonine kinases are located downstream in the signaling pathway within the cells of tumors and tumor vasculature (e.g., RAF/MEK/ERK).

Multiple kinase inhibition targets various signaling pathways in tumor cells and tumor vasculature. For example, preclinical studies have shown that by providing upstream blockade of VEGF and PDGF receptors in the VEGF-signaling pathway as well as downstream blockade of the RAF/MEK/ERK pathway, sorafenib (Nexavar®, Bayer Healthcare Pharmaceuticals) simultaneously decreases both angiogenesis and tumor cell proliferation, which blocks tumor cell growth. Moreover, sorafenib treatment causes a reduction in tumor vasculature in xenograft studies (Chang et al. 2007, Wilhelm et al, 2004). Further, an inhibitor of VEGFR-2 and 3, and PDGFR-β signaling pathways, sorafenib is one of a few VEGF-targeted therapies that have demonstrated clinical utility in RCC treatment (reviewed by Garcia and Rini 2007). In addition, sunitinib malate (Sutent®, Pfizer, Inc.), has been approved for the treatment of advanced RCC. Sunitinib blocks the tyrosine kinase activities of VEGFR2, PDGFRβ, and c-Kit, thereby inhibiting angiogenesis and cell proliferation. This agent also inhibits the phosphorylation of Fms-related tyrosine kinase 3 (FLT3), another receptor tyrosine kinase expressed by some leukemic cells. Finally, cediranib (AZD2171, AstraZeneca) is a potent inhibitor of VEGFR-1, VEGFR-2, VEGFR-3, and in particular VEGFR-2, the predominant receptor through which VEGF exerts its effect on angiogenesis. Cediranib is in clinical development for the treatment of advanced RCC, among other cancers.

Elevated levels of phospho-Akt have been correlated with poor prognosis in RCC (Horiguchi et al. 2003). One of the downstream targets of Akt is the p21 protein, which becomes more stable after phosphorylation (Li et al. 2002). p21 is a prognostic marker in clear cell RCC, in which elevated nuclear and cytosolic p21 levels are indicative of poor prognosis (Weiss et al. 2007).

Another tyrosine kinase receptor associated with RCC is c-Met. Miyata et al. (2006) suggested that phospho c-Met is a predictor of metastasis and survival in RCC patients.

AMPK is a stress-responsive protein kinase that is activated under conditions such as hypoxia. Cross-talk between AMPK and Akt is essential for angiogenesis under hypoxic conditions (Nagata et al. 2003), which would occur during anti-angiogenic therapy. It has been suggested that tumor AMPK activity may stabilize VEGF mRNA under conditions of nutrient deprivation, which suggests that AMPK activation is a pro-angiogenic signal. The activity of another factor, STAT3, is also reportedly induced with hypoxia in RCC leading to VEGF expression (Jung et al. 2005).

There is a complex relationship between GSK3θ activity and sorafenib in melanoma cells (Panka et al. 2008). Sorafenib activates GSK3θ in these cells, which in turn undermines the lethality of the drug in the cells by acting as an anti-apoptotic agent.

SUMMARY OF THE INVENTION

The present invention provides a method for evaluating the efficacy of a treatment regimen in a patient diagnosed with renal cell carcinoma (RCC), wherein the method includes the following steps:

(a) measuring a level of a biomarker in a test sample obtained from a patient undergoing a treatment regimen for RCC, wherein the biomarker is selected from the group consisting of total Akt, total Erk1/2, total Met, total GSK3b, total Hif1a, total p21, total AMPKa1, total VEGF, total PlGF, total VEGFR-1/Flt-1, phosphorylated Akt, phosphorylated Erk1/2, phosphorylated Met, phosphorylated STAT3, phosphorylated GSK3b, and phosphorylated AMPKa1; and (b) evaluating from that level whether the patient is responsive to the treatment regimen.

The method may include measuring a level of two or more biomarkers.

In one embodiment, the biomarkers are selected from the group consisting of total Akt, phosphorylated STAT3, total p21, total VEGF, total PlGF, total VEGFR-1/Flt-1, phosphorylated Erk1/2, p21 and phosphorylated AMPKa1. And in a further embodiment, the phosphorylated AMPKa1 is phosphorylated at amino acid 174 (AMPKa1 p174).

Still further, the measuring step may include measuring levels of a first biomarker and an additional biomarker, wherein the first biomarker is a total form of a biomarker and the additional biomarker is a phosphorylated form of that biomarker. For example, the measuring step may include measuring levels of a pair of a first and an additional biomarker selected from the group consisting of (a) total Akt and phosphorylated Akt; (b) total Erk1/2 and phosphorylated Erk1/2; (c) total Met and phosphorylated Met; (d) total GSK3b and phosphorylated GSK3b; and (e) total AMPKa1 and phosphorylated AMPKa1.

The method of the invention may be used to evaluate the responsiveness or non-responsiveness of a patient to a treatment regimen, e.g., the biomarker level(s) reflect responsiveness or non-responsiveness to a treatment regimen.

The treatment regimen may comprise administration of a therapeutic agent that modulates one or more biological activity and/or one or more signaling pathway and the level(s) of the biomarker indicates modulation of the biological activity and/or signaling pathway by the therapeutic agent. In one embodiment, the signaling pathway is selected from the group consisting of the VEGF-signaling pathway and Raf/Ras/Erk/Mek signaling pathway. Still further, the therapeutic agent is an agonist of a given signaling pathway, or alternatively, the therapeutic agent is an antagonist of a signaling pathway.

In one embodiment, the therapeutic agent is a multi-kinase inhibitor, for example, sorafenib, sunitinib, and cediranib. In a specific embodiment, the therapeutic agent is sorafenib. Still further, the therapeutic agent may cause a reduction in tumor vasculature.

Moreover, the invention provides a method in which the measuring and evaluating steps are carried out by a point of care device and the method further includes providing a report to an end-user, by the device, concerning whether the patient is responsive to the therapeutic regimen.

The method of the present invention may include measuring a baseline level(s) of the biomarker before the therapeutic regimen is initiated, and the evaluating step further comprises comparing the level and the baseline level. Moreover, the method may further comprise measuring an interim level of the biomarker during the therapeutic regimen and the evaluating step further comprises comparing the level, the interim level and the baseline level.

Still further, the evaluating step of the instant method may include comparing the level of the biomarker to a detection cut-off level, wherein the level above the detection cut-off level is indicative of RCC. Alternatively, the evaluating step comprises comparing the level of the biomarker to a detection cut-off level, wherein the level below the detection cut-off level is indicative of RCC.

The measuring step of the method of the instant invention may be conducted on a single sample. Moreover, the measuring step may employ a multiplexed assay. The measuring step(s) may be conducted in a single assay chamber, and the assay chamber may be a single well of an assay plate or the assay chamber may be a cartridge.

The sample used in the method of the present invention may be selected from the group consisting of blood, peripheral blood mononuclear cells (PBMC), isolated blood cells, serum and plasma. Still further, the sample may be biopsy tissue, intestinal mucosa, saliva, cerebral spinal fluid, or urine.

BRIEF DESCRIPTION OF THE DRAWINGS

FIG. 2 illustrates a well 300. Well 300 has a wall 302 having an interior surface 304, counter electrodes 306A and 306B, gaps 308A and 308B, working electrode 310 and assay domains 312.

DETAILED DESCRIPTION OF THE INVENTION

Figure 1:
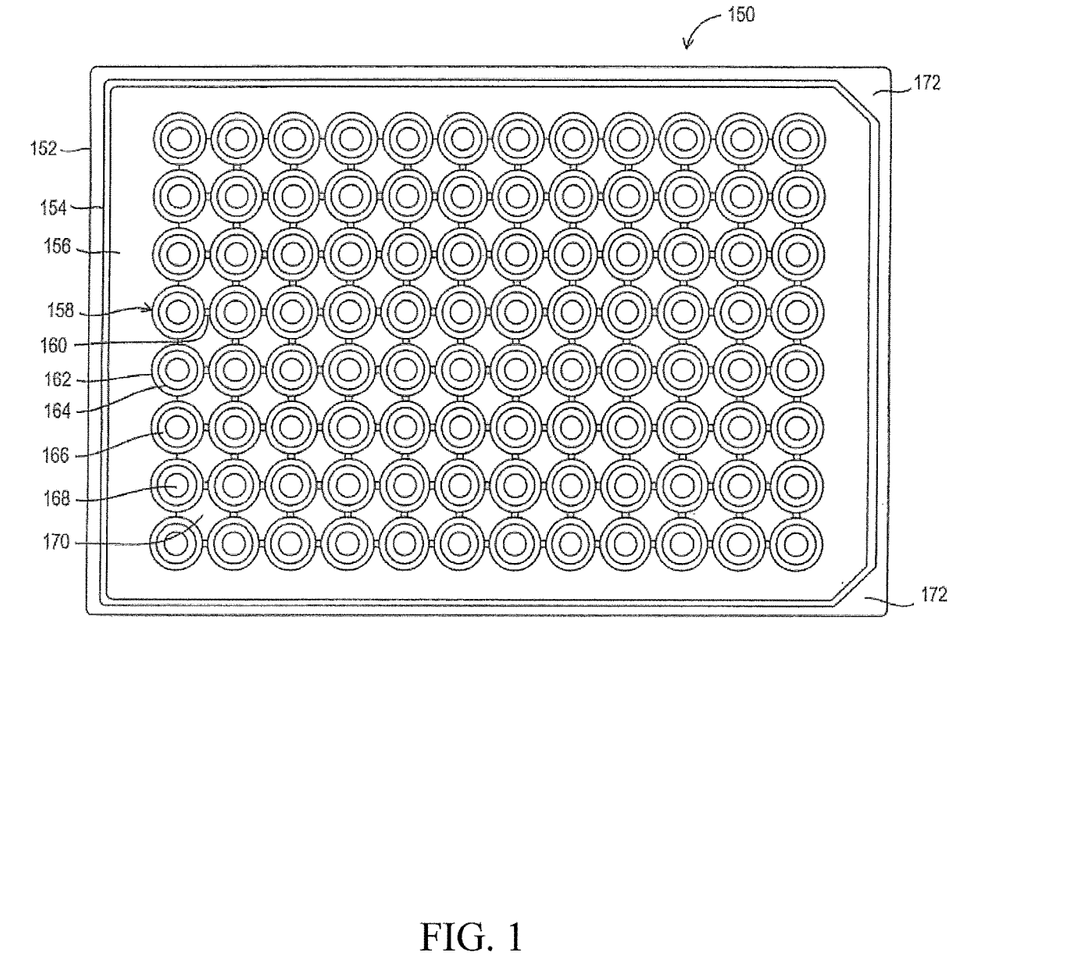
FIG. 1 illustrates a top view of a multi-well assay plate 150 according to one embodiment of the disclosure. Assay plate 150 includes an outer lip 152, an inner lip 154, a top surface 156, and 96 individual wells 158, spacers 160, a wall 162, an interior surface of the wall 164, a counter electrode 166, a working electrode 168, inter-well regions 170 and corner recesses 172.
Figure 2:
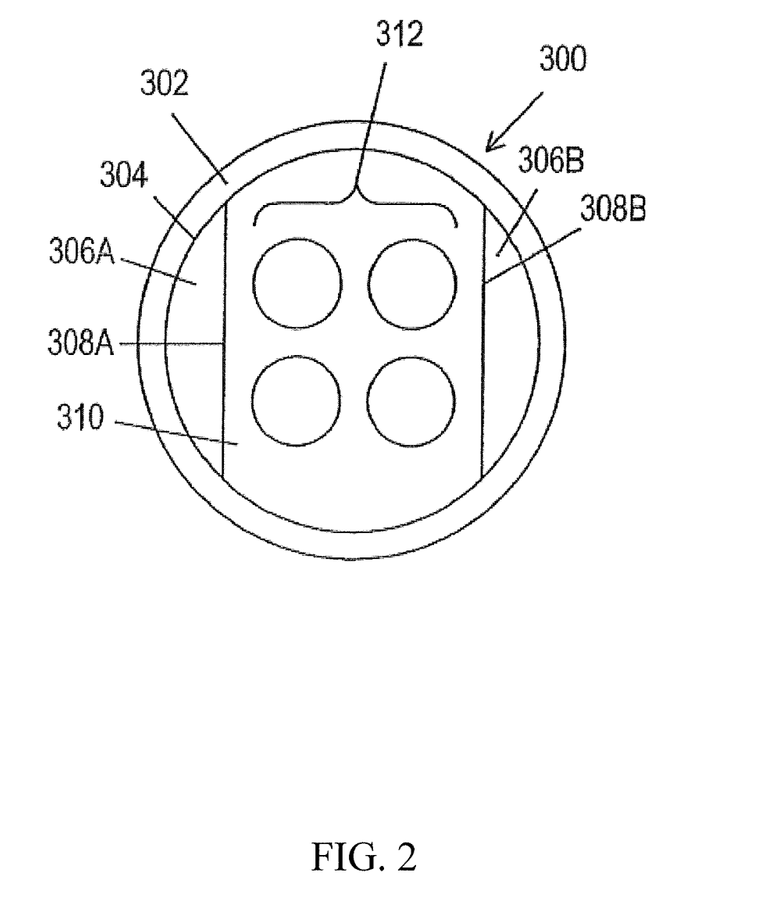
Figure 3:
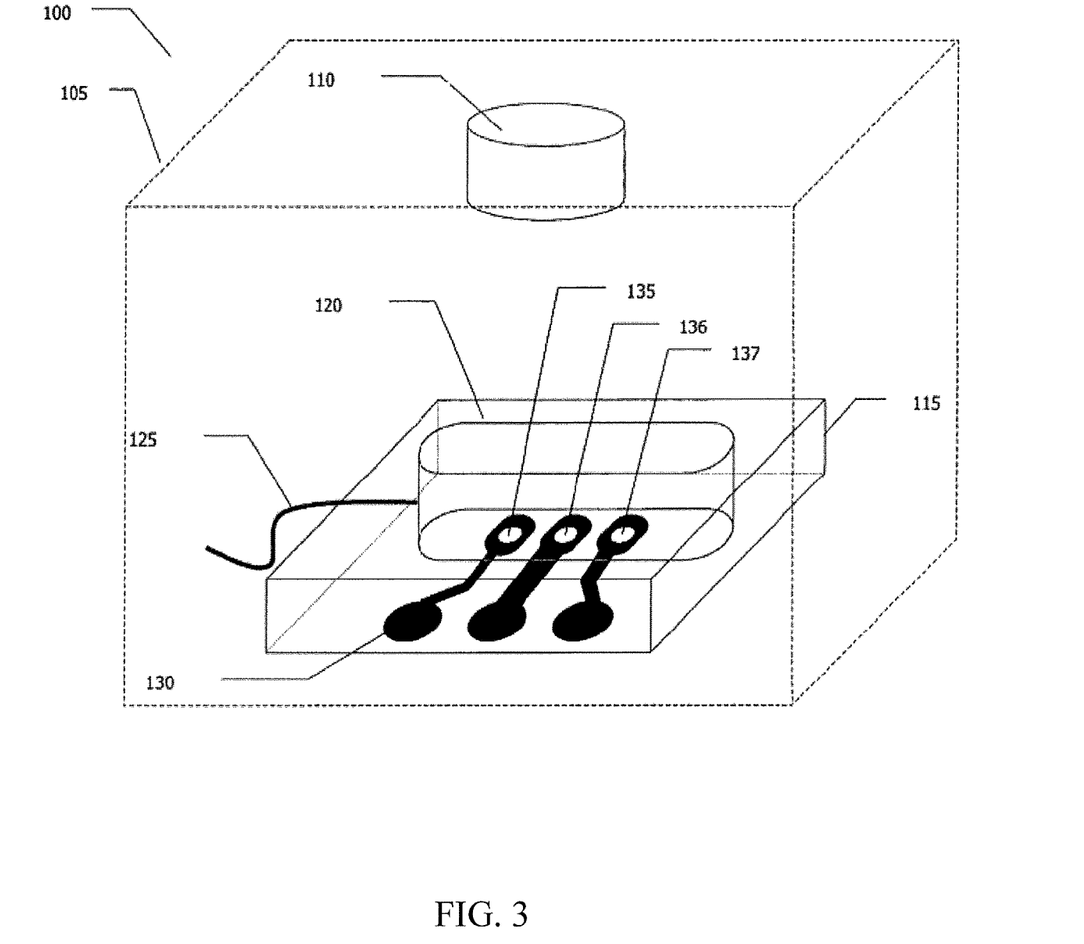
FIG. 3 illustrates a cartridge-based assay module 100. Cartridge-based assay module 100 includes a cartridge reader 105, an optical detector 110, a cartridge 115, a detection chamber 120, an inlet 125, electrical contacts 130, and electrodes 135, 136 and 137.

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. The articles "a" and "an" are used herein to refer to one or to more than one (i.e., to at least one) of the grammatical object of the article. By way of example, "an element" means one element or more than one element.

The present invention includes the use of biomarkers for cancer diagnostics including the use of biomarkers for predicting (prior to treatment) and/or determining (after commencement of treatment) whether a cancer is resistant to a specific course of treatment. Suitable biomarkers including total and/or phosphorylated Akt, Erk1/2, Met, STAT3, GSK30, Hif1α, p21, AMPKa1, VEGF, PlGF, VEGFR-1/Flt-1. The invention includes the use of these biomarkers (or other proteins associated with the VEGF and/or RAF/MEK/ERK signaling pathways) to indicate if treatment with a therapeutic regimen targeting the VEGF signaling pathways and/or the RAF/MEK/ERK pathway results in responsive or non-responsive outcomes. Analysis of human tumor xenograft samples from mice in assays for total and/or phosphorylated Akt, Erk1/2, Met, STAT3, GSK33, Hif1α, p21, AMPKalpha1, VEGF, PlGF, VEGFR-1/Flt-1, and other pharmacodynamic factors shows that these proteins are biomarkers for RCC and that the levels of these proteins can be used to determine the responsiveness or non-responsiveness of cancers (including RCC) to such treatment. Accordingly, the present invention includes a method comprising measuring the levels of one or more of total and/or phosphorylated Akt, Erk1/2, Met, STAT3, GSK30, Hif1α, p21, AMPKa1, VEGF, PlGF, VEGFR-1/Flt-1 to determine if a tumor is responsive and/or non-responsive to treatment with drugs targeting the VEGF or RAF/MEK/ERK pathways (e.g., sorafenib).

Therefore, the invention provides a method for evaluating the efficacy of a treatment regimen in a patient diagnosed with renal cell carcinoma (RCC), said method comprising (a) measuring a level of a biomarker in a test sample obtained from a patient undergoing said treatment regimen for RCC, wherein said biomarker is selected from the group consisting of total Akt, total Erk1/2, total Met, total GSK3b, total Hif1α, total p21, total AMPKa1, total VEGF, total PlGF, total VEGFR-1/Flt-1, phosphorylated Akt, phosphorylated Erk1/2, phosphorylated Met, phosphorylated STAT3, phosphorylated GSK3b, and phosphorylated AMPKa1; and (b) evaluating from said level whether said patient is responsive to said treatment regimen. The method may include measuring a level of two or more biomarkers, or a panel of three or more such biomarkers. The panel may further comprise one or more additional biomarkers selected from the group consisting of carbonic anhydrase IX (CAIX), X-linked inhibitor of apoptosis protein (XIAP), minichromosome maintenance 2 (Mcm2), S100, S100A10, brain fatty acid binding protein (B-FABP), p53, COX-2, B7-H1, B7-H4, osteopontin (OPN), Ki-67, miR-28, miR-185, miR-27 and let-7f-2 (four human micro-RNAs), beta-subunit of human chorionic gonadotropin (b-hCG), thymidine phosphorylase, IMP3, pro-MMP-7, MDR-1/P-glycoprotein, VCAM-1, IFN-α, (Gimenez et al., Future Oncol. (2009) 5(2): 197-205), sVEGFR-3, VEGF-C (Garcia et al., Curr. Opin. Oncol. (2009) 21: 266-71), CA-XII, CXCR3, CXCR4, IGF-1, B7-H3, PD-1, Bcl-2, PTEN, Cyclin A, p27, Skp2, EpCAM/KSA, EMA, E-Cad, alpha-catenin, Cad-6, surviving, EphA2, Smac/DIABLO, PCNA, Caveolin-1, AR, CD44, Annexin II, Gelsolin, Vimentin, CA-125, aberrant DNA methylation, Na—K ATPase α 1 subunit, vitamin D receptor, retinoid X receptor (Lane et al., Urol. Clin. N. Am. (2008) 35: 613-25), gamma-enolase, pyruvate kinase type M2, iNOS, TS, CD10, CD154, AgNOR, Gp200, markers of the mTOR pathway (e.g., phosphorylated protein kinase B (AKT) and phosphorylated S6 kinase) (Tununguntla et al., J. Urol. (2008) 179: 2096-2102), C-reactive protein, CD57+, Fas, APAFI, and DAPK1 (Ljungberg, Curr. Op. Urol. (2007), 17: 303-08.

In one embodiment, the method includes measuring a level of a first biomarker and an additional biomarker, wherein the first biomarker is a total form of a biomarker and the additional biomarker is a phosphorylated form of that biomarker. Diagnosis of the presence or state of a cancer could be based on the absolute levels of one or both of these forms. Alternatively, the diagnosis could be based on the ratio of phosphorylated to total forms (i.e, based on the fraction of a specific biomarker that is present in a phosphorylated form). In one example, the method may include measuring a level of total Akt as the first biomarker and measuring a level of phosphorylated Akt as the additional biomarker. Similarly, the method may comprise measuring one or more of the following pairs of first and additional biomarkers, i.e., total and phosphorylated biomarkers: total Erk1/2 and phosphorylated Erk1/2; total Met and phosphorylated Met; total GSK3b and phosphorylated GSK3b; and total AMPKa1 and phosphorylated AMPKa1.

In one embodiment, the biomarker measured in the method of the present invention is selected from total Akt, phosphorylated STAT3, total p21, total VEGF, total PlGF, total VEGFR-1/Flt-1, phosphorylated Erk1/2, p21 and phosphorylated AMPKa1. In one specific embodiment, the measured biomarker is AMPKa1 phosphorylated at amino acid 174.

The level(s) of the various biomarkers identified herein may reflect the responsiveness or non-responsiveness of a renal cell carcinoma to a given treatment regimen. A response to a therapeutic regimen includes a detectable reduction to some extent of one or more of the symptoms of RCC, including, but not limited to: (1) reduction in the number of cancer cells; (2) reduction in tumor size; (3) inhibition (i.e., slowing to some extent, preferably stopping) of cancer cell infiltration into peripheral organs; (4) inhibition (i.e., slowing to some extent, preferably stopping) of tumor metastasis; (5) inhibition, to some extent, of tumor growth; (6) relieving or reducing to some extent one or more of the symptoms associated with the disorder; and/or (7) increasing, to some extent, the overall survival of a patient relative to that observed for the standard of care for RCC. A response to a therapeutic regimen may also comprise maintenance of a therapeutic benefit, including, but not limited to (1) inhibiting an increase in the number of cancer cells; (2) inhibiting an increase in tumor size; (3) inhibiting cancer cell infiltration into peripheral organs; (4) inhibiting tumor metastases; (5) relieving or reducing to some extent one or more of the symptoms associated with the disorder; and/or (6) inhibiting a recurrence or onset of one or more of the symptoms associated with the disorder.

The therapeutic regimen used in the method of the present invention may include radiation treatment, chemotherapy, treatment with therapeutic drugs, immune system modulation or other therapeutic regimes used in cancer treatment. In one embodiment, the therapeutic regimen comprises administration of a therapeutic agent that modulates one or more biological activities and/or one or more signaling pathways and the level(s) of said one or more biomarkers indicate modulation of said biological activities and/or said signaling pathways by said therapeutic agent. In particular, the signaling pathways may include the VEGF-signaling pathway and Raf/Ras/Erk/Mek signaling pathway and the therapeutic agent may be an agonist or an antagonist of such signaling pathway(s).

The therapeutic regimen may include administration of a therapeutic agent or a combination of therapeutic agents to a patient one or more times over a given time period. For example, if the therapeutic agent is sorafenib, one suitable therapeutic regimen comprises administering the drug twice daily until the patient is no longer clinically benefiting from treatment or until unacceptable toxicity occurs. This treatment regimen may be accompanied by the administration of one or more additional chemotherapeutic agents or palliative agents. The level(s) of biomarkers may be measured before treatment, one or more times during the administration period, and/or after treatment is suspended. If sunitinib is the selected therapeutic agent, one example of a suitable therapeutic regimen comprises administration of the drug once daily for four weeks, followed by a two week period in which sunitinib is not administered to the patient. This cycle may be repeated one or more times. This treatment regimen may also be accompanied by the administration of one or more additional chemotherapeutic agents or palliative agents. The level(s) of biomarkers may be measured at one or more time points in the treatment regimen, e.g., before treatment, one or more times during the four week administration period, and/or after the four week administration period. Therefore, the method may include measuring an interim level of a biomarker during the therapeutic regimen and the evaluating step further comprises comparing that level, the interim level and the baseline level.

In addition, the level of a biomarker may be determined at any time point before and/or after initiation of treatment. In one embodiment, the biomarker is used to gauge the efficacy of a therapeutic regimen. Therefore, the method of the present invention may include measuring a baseline level(s) of a biomarker before a therapeutic regimen is initiated, and the evaluating step further comprises comparing the level and the baseline level. Moreover, the method may further comprise measuring an interim level of the biomarker during the therapeutic regimen and the evaluating step further comprises comparing the level, the interim level and the baseline level.

Alternatively, the measuring step may comprise measuring a level(s) of a biomarker before a therapeutic regimen is initiated to predict whether a RCC will be responsive or non-responsive to a given therapeutic regimen. The method may further comprise modifying the therapeutic regimen based on the level(s) of a biomarker observed during the measuring step, e.g., increasing or decreasing the dosage, frequency, or route of administration of a therapeutic agent, adding an additional therapeutic agent and/or palliative agent to a treatment regimen, or if the therapeutic regimen includes the administration of two or more therapeutic and/or palliative agents, the treatment regimen may be modified to eliminate one or more of the therapeutic and/or palliative agents used in the combination therapy.

Still further, the evaluating step may include comparing the level of a biomarker to a detection cut-off level, wherein a level above the detection cut-off level is indicative of RCC. Alternatively, the evaluating step comprises comparing a level of a biomarker to a detection cut-off level, wherein a level below the detection cut-off level is indicative of RCC.

In one embodiment of the present invention, the level of a biomarker is compared to a detection cut-off level or range, wherein the biomarker level above or below the detection cut-off level (or within the detection cut-off range) is indicative of RCC. Furthermore, the levels of two or more biomarkers may both be used to make a determination. For example, i) having a level of at least one of the markers above or below a detection cut-off level (or within a detection cut-off range) for that marker is indicative of RCC; ii) having the level of two or more (or all) of the markers above or below a detection cut-off level (or within a detection cut-off range) for each of the markers is indicative of RCC; or iii) an algorithm based on the levels of the multiple markers is used to determine if RCC is present.

As described herein, the measured levels of one or more biomarkers may be used to detect or monitor cancer (e.g., RCC) and/or to determine the responsiveness of a cancer to a specific treatment regimen. The specific methods/algorithms for using biomarker levels to make these determinations, as described herein, may optionally be implemented by software running on a computer that accepts the biomarker levels as input and returns a report with the determinations to the user. This software may run on a standalone computer or it may be integrated into the software/computing system of the analytical device used to measure the biomarker levels or, alternatively, into a laboratory information management system (LIMS) into which crude or processed analytical data is entered. In one embodiment, biomarkers are measured in a point-of-care clinical device which carries out the appropriate methods/algorithms for detecting, monitoring or determining the responsiveness of a cancer and which reports such determination(s) back to the user.

In addition, the methods of the present invention may be used in combination with other methods of diagnosing RCC in a patient. In one embodiment, the patient may also be subjected to one or more diagnostic tools designed to detect RCC. For example, imaging methods may be used to provide images of the kidney to look for tumors. In addition, a kidney biopsy may be performed. Imaging methods that may be performed include ultrasound, computed tomography (CT) scan and magnetic resonance imaging (MRI).

As used herein, the term "cancer" is intended to mean a class of diseases characterized by the uncontrolled growth of aberrant cells, including all known cancers, and neoplastic conditions, whether characterized as malignant, benign, soft tissue or solid tumor. In one embodiment, the cancerous condition is metastatic RCC. An estimated 54,390 new cases and an estimated more than 13,000 deaths in the United States of RCC were reported in 2008. Of all kidney tumors, 85% are RCC, and of those patients diagnosed with RCC, 25% present with advanced disease. RCC is frequently an incidental finding via ultrasonography and CT scan. Approximately 15% to 48% of new cases are discovered incidentally and 25% to 30% of patients have metastases at initial presentation.

The assays of the present invention may be conducted by any suitable method. In one embodiment, the measuring step is conducted on a single sample, and it may be conducted in a single assay chamber or assay device, including but not limited to a single well of an assay plate, a single assay cartridge, a single lateral flow device, a single assay tube, etc.

As used herein, the term "sample" is intended to mean any biological fluid, cell, tissue, organ or combinations or portions thereof, which includes or potentially includes a biomarker of a disease of interest. For example, a sample can be a histologic section of a specimen obtained by biopsy, or cells that are placed in or adapted to tissue culture. A sample further can be a subcellular fraction or extract, or a crude or substantially pure nucleic acid molecule or protein preparation. In one embodiment, the samples that are analyzed in the assays of the present invention are blood, peripheral blood mononuclear cells (PBMC), isolated blood cells, serum and plasma. Other suitable samples include biopsy tissue, intestinal mucosa, saliva, cerebral spinal fluid, and urine.

As used herein, a "biomarker" is a substance that is associated with a particular disease. A change in the levels of a biomarker may correlate with the risk or progression of a disease or with the susceptibility of the disease to a given treatment. A biomarker may be useful in the diagnosis of disease risk or the presence of disease in an individual, or to tailor treatments for the disease in an individual (choices of drug treatment or administration regimes and/or to predict responsiveness or non-responsiveness to a particular therapeutic regimen). In evaluating potential drug therapies, a biomarker may be used as a surrogate for a natural endpoint such as survival or irreversible morbidity. If a treatment alters a biomarker that has a direct connection to improved health, the biomarker serves as a "surrogate endpoint" for evaluating clinical benefit A sample that is assayed in the diagnostic methods of the present invention may be obtained from any suitable patient, including but not limited to a patient suspected of having RCC or a patient having a predisposition to RCC. The patient may or may not exhibit symptoms associated with one or more of these conditions.

As used herein, the term "level" refers to the amount, concentration, or activity of a biomarker. The term "level" may also refer to the rate of change of the amount, concentration or activity of a biomarker. A level can be represented, for example, by the amount or synthesis rate of messenger RNA (mRNA) encoded by a gene, the amount or synthesis rate of polypeptide corresponding to a given amino acid sequence encoded by a gene, or the amount or synthesis rate of a biochemical form of a biomarker accumulated in a cell, including, for example, the amount of particular post-synthetic modifications of a biomarker such as a polypeptide, nucleic acid or small molecule. The term can be used to refer to an absolute amount of a biomarker in a sample or to a relative amount of the biomarker, including amount or concentration determined under steady-state or non-steady-state conditions. Level may also refer to an assay signal that correlates with the amount, concentration, activity or rate of change of a biomarker. The level of a biomarker can be determined relative to a control marker or an additional biomarker in a sample. For example, the level of a phosphorylated protein can be presented as the absolute amount of the phosphorylated protein or as the ratio of the amount of the phosphorylated form of the protein to the total amount of the protein.

According to one aspect of the invention, the level(s) of biomarker(s) are measured in samples collected from individuals clinically diagnosed with, suspected of having or at risk of developing RCC. Initial diagnosis may have been carried out using conventional methods, e.g., biopsy or other conventional diagnostic methods. The level(s) of biomarker(s) are also measured in healthy individuals. Specific biomarkers valuable in distinguishing between normal and diseased patients are identified by visual inspection of the data, for example, by visual classification of data plotted on a one-dimensional or multidimensional graph, or by using statistical methods such as characterizing the statistically weighted difference between control individuals and diseased patients and/or by using Receiver Operating Characteristic (ROC) curve analysis. A variety of suitable methods for identifying useful biomarkers and setting detection thresholds/algorithms are known in the art and will be apparent to the skilled artisan.

For example and without limitation, diagnostically valuable biomarkers may be first identified using a statistically weighted difference between control individuals and diseased patients, calculated as $$\frac{D-N}{\sqrt{\sigma_D * \sigma_N}}$$

wherein D is the median level of a biomarker in patients diagnosed as having, for example, kidney cancer, N is the median (or average) of the control individuals, $\sigma_D$ is the standard deviation of D and $\sigma_N$ is the standard deviation of N. The larger the magnitude, the greater the statistical difference between the diseased and normal populations.

According to one embodiment of the invention, biomarkers resulting in a statistically weighted difference between control individuals and diseased patients of greater than, e.g., 1, 1.5, 2, 2.5 or 3 could be identified as diagnostically valuable markers.

Another method of statistical analysis for identifying biomarkers is the use of z-scores, e.g., as described in Skates et al. (2007) Cancer Epidemiol. Biomarkers Prev. 16(2):334-341.

Another method of statistical analysis that can be useful in the inventive methods of the invention for determining the efficacy of particular candidate analytes, such as particular biomarkers, for acting as diagnostic marker(s) is ROC curve analysis. An ROC curve is a graphical approach to looking at the effect of a cut-off criterion, e.g., a cut-off value for a diagnostic indicator such as an assay signal or the level of an analyte in a sample, on the ability of a diagnostic to correctly identify positive or negative samples or subjects. One axis of the ROC curve is the true positive rate (TPR, i.e., the probability that a true positive sample/subject will be correctly identified as positive, or alternatively, the false negative rate (FNR=1−TPR, the probability that a true positive sample/subject will be incorrectly identified as a negative). The other axis is the true negative rate, i.e., TNR, the probability that a true negative sample will be correctly identified as a negative, or alternatively, the false positive rate (FPR=1−TNR, the probability that a true negative sample will be incorrectly identified as positive). The ROC curve is generated using assay results for a population of samples/subjects by varying the diagnostic cut-off value used to identify samples/subjects as positive or negative and plotting calculated values of TPR or FNR and TNR or FPR for each cut-off value. The area under the ROC curve (referred to herein as the AUC) is one indication of the ability of the diagnostic to separate positive and negative samples/subjects. In one embodiment, a biomarker provides an AUC≤0.7. In another embodiment, a biomarker provides an AUC≥0.8. In another embodiment, a biomarker provides an AUC≥0.9.

Diagnostic indicators analyzed by ROC curve analysis may be a level of an analyte, e.g., a biomarker, or an assay signal. Alternatively, the diagnostic indicator may be a function of multiple measured values, for example, a function of the level/assay signal of a plurality of analytes, e.g., a plurality of biomarkers, or a function that combines the level or assay signal of one or more analytes with a patient's scoring value that is determined based on visual, radiological and/or histological evaluation of a patient. The multi-parameter analysis may provide more accurate diagnosis relative to analysis of a single marker.

Candidates for a multi-analyte panel could be selected by using criteria such as individual analyte ROC areas, median difference between groups normalized by geometric inter-quartile range (IQR) etc. The objective is to partition the analyte space to improve separation between groups (for example, normal and disease populations) or to minimize the misclassification rate.

One approach is to define a panel response as a weighted combination of individual analytes and then compute an objective function like ROC area, product of sensitivity and specificity, etc. See e.g., WO 2004/058055, as well as US2006/0205012, the disclosures of which are incorporated herein by reference in their entireties.

Biomarker levels may be measured using any of a number of techniques available to the person of ordinary skill in the art, e.g., direct physical measurements (e.g., mass spectrometry) or binding assays (e.g., immunoassays, agglutination assays and immunochromatographic assays). The method may also comprise measuring a signal that results from a chemical reactions, e.g., a change in optical absorbance, a change in fluorescence, the generation of chemiluminescence or electrochemiluminescence, a change in reflectivity, refractive index or light scattering, the accumulation or release of detectable labels from the surface, the oxidation or reduction or redox species, an electrical current or potential, changes in magnetic fields, etc. Suitable detection techniques may detect binding events by measuring the participation of labeled binding reagents through the measurement of the labels via their photoluminescence (e.g., via measurement of fluorescence, time-resolved fluorescence, evanescent wave fluorescence, up-converting phosphors, multi-photon fluorescence, etc.), chemiluminescence, electrochemiluminescence, light scattering, optical absorbance, radioactivity, magnetic fields, enzymatic activity (e.g., by measuring enzyme activity through enzymatic reactions that cause changes in optical absorbance or fluorescence or cause the emission of chemiluminescence). Alternatively, detection techniques may be used that do not require the use of labels, e.g., techniques based on measuring mass (e.g., surface acoustic wave measurements), refractive index (e.g., surface plasmon resonance measurements), or the inherent luminescence of an analyte.

Binding assays for measuring biomarker levels may use solid phase or homogenous formats. Suitable assay methods include sandwich or competitive binding assays. Examples of sandwich immunoassays are described in U.S. Pat. Nos. 4,168,146 and 4,366,241, both of which are incorporated herein by reference in their entireties. Examples of competitive immunoassays include those disclosed in U.S. Pat. Nos. 4,235,601, 4,442,204 and 5,208,535, each of which are incorporated herein by reference in their entireties.

Multiple biomarkers may be measured using a multiplexed assay format, e.g., multiplexing through the use of binding reagent arrays, multiplexing using spectral discrimination of labels, multiplexing of flow cytometric analysis of binding assays carried out on particles, e.g., using the Luminex® system. Suitable multiplexing methods include array based binding assays using patterned arrays of immobilized antibodies directed against the biomarkers of interest. Various approaches for conducting multiplexed assays have been described (See e.g., US 20040022677; US 20050052646; US 20030207290; US 20030113713; US 20050142033; and US 20040189311, each of which is incorporated herein by reference in their entireties. One approach to multiplexing binding assays involves the use of patterned arrays of binding reagents, e.g., U.S. Pat. Nos. 5,807,522 and 6,110,426; Delehanty J-B., Printing functional protein microarrays using piezoelectric capillaries, Methods Mol. Bio. (2004) 278: 135-44; Lue R Y et al., Site-specific immobilization of biotinylated proteins for protein microarray analysis, Methods Mol. Biol. (2004) 278: 85-100; Lovett, Toxicogenomics: Toxicologists Brace for Genomics Revolution, Science (2000) 289: 536-537; Berns A, Cancer: Gene expression in diagnosis, nature (2000), 403, 491-92; Walt, Molecular Biology: Bead-based Fiber-Optic Arrays, Science (2000) 287: 451-52 for more details). Another approach involves the use of binding reagents coated on beads that can be individually identified and interrogated. See e.g., WO 9926067, which describes the use of magnetic particles that vary in size to assay multiple analytes; particles belonging to different distinct size ranges are used to assay different analytes. The particles are designed to be distinguished and individually interrogated by flow cytometry. Vignali has described a multiplex binding assay in which 64 different bead sets of microparticles are employed, each having a uniform and distinct proportion of two dyes (Vignali, D. A A, "Multiplexed Particle-Based Flow Cytometric Assays" J. ImmunoL Meth. (2000) 243: 243-55). A similar approach involving a set of 15 different beads of differing size and fluorescence has been disclosed as useful for simultaneous typing of multiple pneumococcal serotypes (Park, M. K et al., "A Latex Bead-Based Flow Cytometric Immunoassay Capable of Simultaneous Typing of Multiple Pneumococcal Serotypes (Multibead Assay)" Clin. Diag. Lab ImmunoL (2000) 7: 4869).

Bishop, J E et al. have described a multiplex sandwich assay for simultaneous quantification of six human cytokines (Bishop, L E. et al., "Simultaneous Quantification of Six Human Cytokines in a Single Sample Using Microparticle-based Flow Cytometric Technology," Clin. Chem (1999) 45:1693-1694).

A diagnostic test may be conducted in a single assay chamber, such as a single well of an assay plate or an assay chamber that is an assay chamber of a cartridge. The assay modules, e.g., assay plates or cartridges or multi-well assay plates), methods and apparatuses for conducting assay measurements suitable for the present invention are described for example, in US 20040022677; US 20050052646; US 20050142033; US 20040189311, each of which is incorporated herein by reference in their entireties. Assay plates and plate readers are now commercially available (MULTI-SPOT® and MULTI-ARRAY® plates and SECTOR® instruments, Meso Scale Discovery®, a division of Meso Scale Diagnostics, LLC, Gaithersburg, Md.).

The following non-limiting examples serve to illustrate rather than limit the present invention.

Examples

Measurement of Biomarkers Indicative of Sorafenib Resistance in the Treatment of RCC A panel of biomarkers was measured in RCC xenograft tissue extracts from mice. The mice were implanted with human 786-0 RCC cells and the cells were allowed to grow until a tumor of approximately 12 mm diameter was formed. The "Set A" group of mice received no drug treatment prior to removal of the xenograft tissue. The other two groups of mice—"Set C" and "Set D"—were treated with sorafenib prior to removal of the xenograft tissue. The "Set C" group showed sensitivity to the drug, i.e., the tumor size decreased. The "Set D" developed resistance to the drug and the tumor size increased to 16 mm in diameter during treatment.

Multiplex immunoassay kits were used for detection of total and/or phosphorylated biomarkers (supplied by Meso Scale Diagnostics, LLC, Gaithersburg, Md.). Levels of each biomarker were determined by calibration of the assays with were either purified calibrator proteins or using control cell lysates from appropriately treated cultured cell lines (e.g., cells subjected to conditions known to induce or reduce levels of a specific biomarker). Calibration curves were derived by testing serial dilutions of the calibrator lysates or purified proteins. Levels of biomarkers in test samples were back-calculated from the calibration curves and were expressed in terms of wt. of protein per weight of tissue extract (for purified calibrators) or in terms of weight of crude control lysate protein per well (for lysate calibrators). Titrations of tumor extracts were carried out to determine the linearity of the assay response to sample dilution and to select the sample dilution that would be appropriate to use for each assay panel.

In general, the assay format was as follows, with minor alterations for specific assay panels as indicated in the assay protocols provided with each assay kit (supplied by Meso Scale Diagnostics, LLC): (1) block MSD MULTI-SPOT® plate for 1 hour with appropriate MSD® blocking solution and wash; (2) add 25 μl assay diluent to each well, if specified; (3) add 25 μl calibrator, or sample (diluted as appropriate) to each well; (4) incubate with shaking for 1-3 hours (time as specified) and wash the well; (5) add 25 μl labeled detection antibody solution to each well; (6) incubate with shaking for 1-2 hours (time as specified) and wash the well; (7) add 150 μl MSD read buffer to each well; (8) read plate immediately on MSD SI6000 Reader (supplied by Meso Scale Diagnostics, LLC). The results of these studies are summarized in Tables 1 and 2 below.

A significant difference in the level of a biomarker in sorafenib sensitive and resistant tumors (see the far-right column in Table 2) indicates that the marker can be used to characterize the RCC tumor as responsive or non-responsive. The use of specific profiles of the levels of multiple markers (as shown in Tables 1 and 2) provides a signature pattern of changes in the levels of specific biomarkers that further strengthens the characterization of RCC tumors as sorafenib-responsive or non-responsive. The measurement of this set of markers (or individual markers or subsets of markets selected from the set of markers) could greatly improve the effectiveness of treatment with this therapeutic agent.

TABLE 1

The average and standard deviations for the levels of each tested biomarker for tumor tissue extracts from mice in groups A, C and D. The extracts were diluted to the following concentrations (in terms of weight of extract protein per well) prior to analysis: 0.5 ug total protein/well for phospho/total Akt, phospho/total Erk1/2, total p38 phospho/total Met, and p21; 1 ug protein/well for phospho/total MEK1/2, phospho/total GSK3β, and phospho/total AMPKα1; 2 ug protein/well for phosphoSTAT3; 2.5 ug protein/well for phospho/total Jnk, VEGF, bFGF, PlGF, and VEGFR-1; and 4 ug protein/well for Hif1α. The biomarker levels are expressed in the units shown in the leftmost column.

| | | Marker Concentrations +/− SD | | |
|---|---|---|---|---|
| | | Tumor Group A (untreated) | Tumor Group C (treated) | Tumor Group D (resistant) |
| Akt (ng calibrator lysate protein/well) | Total | 143 +/− 25 | 142 +/− 43 | 93 +/− 25 |
| | Phospho | 312 +/− 58 | 348 +/− 85 | 354 +/− 84 |
| Erk1/2 (ng calibrator lysate protein/well) | Total | 462 +/− 81 | 577 +/− 212 | 486 +/− 306 |
| | Phospho | 106 +/− 27 | 102 +/− 45 | 206 +/− 103 |
| Jnk (ng calibrator lysate protein/well) | Total | 730 +/− 193 | 983 +/− 356 | 878 +/− 231 |
| | Phospho | 91 +/− 27 | 74 +/− 29 | 110 +/− 22 |
| Met (ng calibrator lysate protein/well) | Total | 406 +/− 166 | 850 +/− 375 | 595 +/− 137 |
| | Phospho | 15 +/− 7 | 34 +/− 7 | 41 +/− 6 |
| Gsk3b (ng calibrator lysate protein/well) | Total | 4360 +/− 55 | 3771 +/− 1491 | 3829 +/− 1058 |
| | Phospho | 935 +/− 261 | 1188 +/− 446 | 1474 +/− 294 |
| Mek1/2 (ng calibrator lysate protein/well) | Total | 332 +/− 59 | 350 +/− 90 | 359 +/− 103 |
| | Phospho | 90 +/− 8 | 116 +/− 21 | 113 +/− 24 |
| AMPKα1 (pg/ug tumor protein) | Total | 20 +/− 2 | 29 +/− 13 | 26 +/− 10 |
| | p174 | 5.5 +/− 0.6 | 7.3 +/− 4.4 | 3.8 +/− 0.9 |
| | p285 | 17 +/− 2 | 29 +/− 15 | 19 +/− 5 |
| STAT3 (ng calibrator lysate protein/well) | Phospho | 60 +/− 32 | 65 +/− 16 | 41 +/− 10 |
| Hif1a (ng calibrator lysate protein/well) | Total | 14 +/− 3 | 19 +/− 3 | 14 +/− 3 |
| p38 (ng calibrator lysate protein/well) | Total | 529 +/− 174 | 449 +/− 266 | 428 +/− 227 |
| bFGF (pg/ug tumor protein) | Total | 2.7 +/− 0.8 | 2.1 +/− 0.6 | 2.6 +/− 1.3 |
| VEGF (pg/ug tumor protein) | Total | 0.68 +/− 0.51 | 11.4 +/− 3.7 | 26 +/− 15 |
| PlGF (pg/ug tumor protein) | Total | 0.015 +/− 0.006 | 0.083 +/− 0.031 | 0.144 +/− 0.073 |
| VEGFR-1 (pg/ug tumor protein) | Total | 0.05 +/− 0.03 | 0.26 +/− 0.08 | 0.39 +/− 0.14 |
| p21 (pg/ug tumor protein) | Total | 1.6 +/− 0.4 | 1.1 +/− 0.3 | 2.2 +/− 0.9 |

TABLE 2

Comparison of the relative level of each biomarker in the three groups of test mice: untreated (A), treated and sensitive to sorafenib (C) and treated and resistant to sorafenib (D). The presence of a significantly different level of a biomarker in one group relative to another is shown through the use of an arrow in the appropriate table cell. For example, an arrow pointing upward in the "Resistant vs. Sensitive" column for a specific marker, indicates that the sorafenib-resistant mice had higher levels of that marker than the sensitive mice. The number of arrows is indicative of the magnitude of the change.

| | | Sensitive (C) vs UnTreated (A) | Resistant (D) vs Untreated (A) | Resistant (D) vs Sensitive (C) |
|---|---|---|---|---|
| Akt | Total | no diff | ↓ | ↓ |
| | Phospho | no diff | no diff | no diff |
| Erk1/2 | Total | no diff | no diff | no diff |
| | Phospho | no diff | ↑ | ↑ |
| Jnk | Total | no diff | no diff | no diff |
| | Phospho | no diff | no diff | no diff |
| Met | Total | ↑ | no diff | no diff |
| | Phospho | ↑↑ | ↑↑ | no diff |
| Gsk3b | Total | no diff | no diff | no diff |
| | Phospho | no diff | ↑ | no diff |
| Mek1/2 | Total | no diff | no diff | no diff |
| | Phospho | no diff | no diff | no diff |
| AMPKa1 | Total | no diff | no diff | no diff |
| | p174 | no diff | ↓ | ↓ |
| | p285 | no diff | no diff | no diff |
| STAT | Phospho | no diff | no diff | ↓ |
| Hif1a | Total | no diff | no diff | no diff |
| p38 | Total | no diff | no diff | no diff |
| bFGF | Total | no diff | no diff | no diff |
| VEGF | Total | ↑↑ | ↑↑ | ↑ |
| PlGF | Total | ↑↑ | ↑↑ | ↑ |
| VEGFR-1 | Total | ↑↑ | ↑↑ | ↑ |
| p21 | Total | no diff | no diff | ↑ |

Various publications and test methods are cited herein, the disclosures of which are incorporated herein by reference in their entireties, In cases where the present specification and a document incorporated by reference and/or referred to herein include conflicting disclosure, and/or inconsistent use of terminology, and/or the incorporated/referenced documents use or define terms differently than they are used or defined in the present specification, the present specification shall control.

REFERENCES

Bachelder R E, Crago A, Chung J, Wendt M A, Shaw L M, Robinson G, Mercurio A M. (2001) Vascular endothelial growth factor is an autocrine survival factor for neuropilin-expressing breast carcinoma cells. Cancer Res. 1; 61(15):5736-40.

Chang Y S, Adnane J, Trail P A, Levy J, Henderson A, Xue D, Bortolon E, Ichetovkin M, Chen C, McNabola A, Wilkie D, Carter C A, Taylor I C, Lynch M, Wilhelm S. (2007) Sorafenib (BAY 43-9006) inhibits tumor growth and vascularization and induces tumor apoptosis and hypoxia in RCC xenograft models. Cancer Chemother. Pharmacol. 59(5):561-74.

Chen Z, Trotman L C, Shaffer D, Lin H K, Dotan Z A, Niki M, Koutcher J A, Scher H I, Ludwig T, Gerald W, Cordon-Cardo C, Pandolfi P P. (2005) Crucial role of p53-dependent cellular senescence in suppression of Pten-deficient tumorigenesis. Nature 436(7051):725-30.

Fan Y, Borowsky A D, Weiss R H. (2003) An antisense oligodeoxynucleotide to p21(Waf1/Cip1) causes apoptosis in human breast cancer cells. Mol Cancer Ther. 2(8): 773-82.

Garcia J A, Rini B I. (2007) Recent progress in the management of advanced renal cell carcinoma. C A Cancer J. Clin. March-April; 57(2): 112-25.

Horiguchi A, Oya M, Uchida A, Marumo K, Murai M. (2003) Elevated Akt activation and its impact on clinicopathological features of renal cell carcinoma. J. Urol. 169(2):710-13.

Jung J E, Lee H G, Cho I H, Chung D H, Yoon S H, Yang Y M, Lee J W, Choi S, Park J W, Ye S K, Chung M H. (2005) STAT3 is a potential modulator of HIF-1-mediated VEGF expression in human renal carcinoma cells. FASEB J. 19(10):1296-8.

Kummar S, Kinders R, Rubinstein L, Parchment R E, Murgo A J, Collins J, Pickeral O, Low J, Steinberg S M, Gutierrez M, Yang S, Helman L, Wiltrout R, Tomaszewski J E, Doroshow J H. (2007) Compressing drug development timelines in oncology using phase '0' trials. Nat Rev Cancer. 7(2):131-39.

Lee T H, Seng S, Sekine M, Hinton C, Fu Y, Avraham H K, Avraham S. (2007) Vascular endothelial growth factor mediates intracrine survival in human breast carcinoma cells through internally expressed VEGFR1/FLT1. PLoS Med. 4(6):e186.

Li Y, Dowbenko D, Lasky L A. (2002) AKT/PKB phosphorylation of p21Cip/WAF1 enhances protein stability of p21Cip/WAF1 and promotes cell survival. J Biol Chem. 277(13):11352-61.

Masood R, Cai J, Zheng T, Smith D L, Hinton D R, Gill P S. (2001) Vascular endothelial growth factor (VEGF) is an autocrine growth factor for VEGF receptor-positive human tumors. Blood. 98(6):1904-13.

Miyata Y, Kanetake H, Kanda S. (2006) Presence of phosphorylated hepatocyte growth factor receptor/c-Met is associated with tumor progression and survival in patients with conventional renal cell carcinoma. Clin Cancer Res. 12(16):4876-81.

Motoshima H, Goldstein B J, Igata M, Araki E. J. (2006) AMPK and cell proliferation-AMPK as a therapeutic target for atherosclerosis and cancer. Physiol. 574(Pt 1):63-71.

Murphy D A, Makonnen S, Lassoued W, Feldman M D, Carter C, Lee W M. (2006) Inhibition of tumor endothelial ERK activation, angiogenesis, and tumor growth by sorafenib (BAY43-9006). Am J Pathol. 169(5): 1875-85.

Nagata D. Mogi M, Walsh K. (2003) AMP-activated protein kinase (AMPK) signaling in endothelial cells is essential for angiogenesis in response to hypoxic stress. J Biol Chem. 278(33):31000-6.

Panka D J, Cho D C, Atkins M B, Mier J W. (2008) GSK-3beta inhibition enhances sorafenib-induced apoptosis in melanoma cell lines. J Biol Chem. 283(2):726-32.

Rini B I. (2007) Vascular endothelial growth factor-targeted therapy in renal cell carcinoma: current status and future directions. Clin Cancer Res. 13(4): 1098-106.

Waltenberger J, Claesson-Welsh L, Siegbahn A, Shibuya M, Heldin C H. (1994) Different signal transduction properties of KDR and Flt1, two receptors for vascular endothelial growth factor. J Biol Chem. 269(43):26988-95.

Weiss R H (2003) p21Waf1/Cip1 as a therapeutic target in breast and other cancers. Cancer Cell. 4(6):425-9.

Weiss R H, Borowsky A D, Seligson D, Lin P Y, Dillard-Telm L, Belldegrun A S, Figlin R A, Pantuck A D. (2007) p21 is a prognostic marker for renal cell carcinoma: implications for novel therapeutic approaches. J Urol. 177(1):63-8; discussion 68-9.

Wilhelm S M, Carter C, Tang L, Wilkie D, McNabola A, Rong H, Chen C, Zhang X, Vincent P, McHugh M, Cao Y, Shujath J, Gawlak S, Eveleigh D, Rowley B, Liu L, Adnane L, Lynch M, Auclair D, Taylor I, Gedrich R, Voznesensky A, Riedl B, Post L E, Bollag G, Trail P A. (2004) BAY 43-9006 exhibits broad spectrum oral antitumor activity and targets the RAF/MEK/ERK pathway and receptor tyrosine kinases involved in tumor progression and angiogenesis. Cancer Res. 64(19):7099-109.

What is claimed:

1. A method for evaluating a first treatment regimen in a patient diagnosed with renal cell carcinoma (RCC), said method comprising (a) measuring levels of biomarkers in a test sample obtained from a patient after administration of the first treatment regimen, the first treatment regimen comprising sorafenib, wherein said biomarkers are total Akt, phosphorylated Erk1/2, and AMPKa1 phosphorylated at amino acid 174;

(b) evaluating from said levels whether said patient is responsive or resistant to said first treatment regimen, wherein the patient is resistant to said first treatment regimen if the measured level of total Akt is lower than that in an untreated patient or that in a patient subjected to said first treatment regimen whose RCC is sensitive to said first treatment regimen, wherein the patient is resistant to said first treatment regimen if the measured level of phosphorylated Erk1/2 is higher than that in an untreated patient or that in a patient treated with said first treatment regimen whose RCC is sensitive to said first treatment regimen, and wherein the patient is resistant to said first treatment regimen if the measured level of AMPKa1 phosphorylated at amino acid 174 is lower than that in an untreated patient or that in a patient subjected to said first treatment regimen whose RCC is sensitive to said first treatment regimen;

(c) identifying the patient as being resistant to said first treatment regimen or not resistant to said first treatment regimen, and performing one of step (d) or step (e), (d) administering a second treatment regimen if the patient is resistant to said first treatment regimen, wherein said second treatment regimen is administration of a therapeutic agent that modulates one of a VEGF-signaling pathway and a Raf/Ras/Erk/Mek signaling pathway, or (e) continuing administration of said first treatment regimen if the patient is not resistant to said first treatment regimen.

2. The method of claim 1, wherein said method measures said levels using an immunoassay.

3. The method of claim 1, wherein said method measures said levels using a multi-well assay plate including a plurality of assay wells used in an assay conducted in said method, said plurality of assay wells configured to measure said levels of biomarkers in said sample.

4. The method of claim 3, wherein a well of said assay plate comprises a plurality of assay domains, at least two of said assay domains comprising reagents for measuring different biomarkers.

5. The method of claim 1, wherein said method measures said levels using an assay cartridge for conducting a plurality of assays, said cartridge comprising a flow cell having an inlet, an outlet or a detection chamber, said inlet, detecting chamber, or outlet defining a flow path through said flow cell, said detection chamber configured to measure said levels of biomarkers in said sample.

6. The method of claim 1, wherein said measurement step comprises the use of one or more additional assay reagents used in said assay, said one or more additional assay reagents provided in one or more vials, containers, or compartments of said method.

7. The method of claim 1, wherein said measurement step comprises the use of one or more vials, containers, or compartments, containing a set of labeled detection antibodies specific for said human analytes and in one or more vials, containers, or compartments, a set of calibrator proteins.

8. The method of claim 7 wherein said detection antibodies are labeled with an electrochemiluminescent (ECL) label.

9. The method of claim 7 wherein said method further comprises the use of an ECL read buffer.

10. The method of claim 1 wherein said biomarkers further comprise phosphorylated STAT3.

11. The method of claim 1 wherein said biomarkers further comprise total p21.

12. The method of claim 10, wherein the patient is resistant to said first treatment regimen if the measured level of phosphorylated STAT3 is lower than that in a patient subjected to said first treatment regimen whose RCC is sensitive to said first treatment regimen.

13. The method of claim 11, wherein the patient is resistant to said first treatment regimen if the measured level of total p21 is higher than that in a patient subjected to said first treatment regimen whose RCC is sensitive to said first treatment regimen.

* * * * *